(12) United States Patent
Muraishi et al.

(10) Patent No.: US 7,545,501 B2
(45) Date of Patent: Jun. 9, 2009

(54) SENSOR UNIT FOR ASSAY AND PRISM

(75) Inventors: Katsuaki Muraishi, Kanagawa (JP); Hitoshi Shimizu, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 254 days.

(21) Appl. No.: 11/723,232

(22) Filed: Mar. 19, 2007

(65) Prior Publication Data

US 2008/0088847 A1  Apr. 17, 2008

(30) Foreign Application Priority Data

Mar. 20, 2006  (JP) .............................. 2006-076375

(51) Int. Cl.
*G01N 21/55* (2006.01)
(52) U.S. Cl. ..................... 356/445; 356/246; 422/82.05
(58) Field of Classification Search .................. 356/445
See application file for complete search history.

(56) References Cited

U.S. PATENT DOCUMENTS

| 5,164,589 | A | 11/1992 | Sjödin |
| 5,313,264 | A | 5/1994 | Ivarsson et al. |
| 7,030,988 | B2* | 4/2006 | Kubo et al. ................. 356/445 |
| 7,193,703 | B2* | 3/2007 | Hakamata et al. ........... 356/246 |
| 2006/0068489 | A1* | 3/2006 | Muraishi et al. ......... 435/287.1 |
| 2006/0078985 | A1* | 4/2006 | Ogura et al. ............. 435/287.2 |
| 2006/0146333 | A1* | 7/2006 | Hakamata et al. ........... 356/445 |
| 2006/0197954 | A1* | 9/2006 | Ogura et al. ................. 356/445 |
| 2006/0252158 | A1* | 11/2006 | Ogura ......................... 436/514 |
| 2006/0263263 | A1* | 11/2006 | Shimizu ..................... 422/100 |
| 2006/0263874 | A1* | 11/2006 | Kunuki et al. ............ 435/287.2 |
| 2007/0004030 | A1* | 1/2007 | Ogura et al. ............. 435/287.2 |

FOREIGN PATENT DOCUMENTS

JP  3294605 B2  4/2002

* cited by examiner

*Primary Examiner*—Roy Punnoose
(74) *Attorney, Agent, or Firm*—Sughrue Mion, PLLC

(57) ABSTRACT

A sensor unit is for use in a surface plasmon resonance (SPR) assay apparatus having an assay stage. A total reflection prism is supported on a stage surface of the assay stage, and has a sensing surface positioned on an upper surface thereof. The sensing surface receives illuminating light applied thereto to reflect the illuminating light. The assay apparatus receives the illuminating light reflected by the sensing surface, for measuring reaction of a sample. Two engageable ridges are disposed on first and second lateral faces of the prism which are so positioned that the sensing surface is disposed between, and keep the prism positioned on the stage surface by engagement with a retention mechanism of the assay apparatus. Furthermore, a grip portion is formed at a first end of the prism, and adapted to holding of the prism.

12 Claims, 8 Drawing Sheets

SENSOR UNIT FOR ASSAY AND PRISM

BACKGROUND OF THE INVENTION

1. Field of the Invention

The present invention relates to a sensor unit for assay and a prism. More particularly, the present invention relates to a sensor unit for assay and a prism, in which a light path of photo detection can be prevented from offsetting in the course of assay.

2. Description Related to the Prior Art

An assay apparatus for assay in utilizing attenuated total reflection is used for various kinds of studies in a biochemical field or the like, for example to study interaction of protein, DNA and various biomaterials, and to select candidate drugs by screening. Also, the technique is useful in the fields of the clinical medicine, food industries and the like.

A surface plasmon resonance (SPR) sensor is known as an assay apparatus in utilizing attenuated total reflection. Surface plasmon is a term to mean the compressional wave created on the surface of the metal and included in plasmon as quantized expression of the compressional wave. Free electrons in a metal vibrate to generate the compressional wave.

U.S. Pat. Nos. 5,164,589 and 5,313,264 (corresponding to JP-B 3294605) disclose an SPR assay apparatus with Kretschmann configuration. In the assay apparatus, the sensing surface is positioned opposite to an interface where a metal thin film is connected with a prism as dielectric block. Light is applied through the prism to the sensing surface. Total reflection of the illuminating light occurs. Reaction of samples is assayed by detecting the SPR on the sensing surface.

Biomaterials as samples are handled as sample fluid which contains a sample and fluid medium to which the sample is added, for the purpose of preventing modification or deactivation due to drying. Examples of fluid media include physiological saline water, pure water, buffer liquids and the like. The assay apparatus of U.S. Pat. Nos. 5,164,589 and 5,313,264 (corresponding to JP-B 3294605) is used to detect and study interaction between biomaterials. The flow channel is formed for flow of the sample fluid in contact with the sensing surface. Note that linker film is formed on the sensing surface for immobilizing a sample as ligand. In a sample immobilization, ligand fluid is introduced in the flow channel to immobilize the ligand on the linker film. In an assay after this, analyte fluid is introduced in the flow channel to react ligand on the analyte.

A flow cell with a flow channel and the prism are disposed on an assay stage of the assay apparatus. A sensor unit of a chip type is set on the assay stage, having thin film of metal formed on a glass substrate. A pump is connected with the flow channel by a conduit, valve and the like, to supply the flow channel with the sample fluid from a fluid reservoir. However, a problem of contamination is likely to occur in that the sample may stick on the inside of the conduit and will mix with the sample fluid.

To solve such a problem, a type of the assay apparatus is suggested in which pipette devices are used. Each of the pipette devices includes a pipette head and a pipette tip secured to the pipette head removably. The pipette devices dispense the sample fluid into the flow channel. It is possible in the assay apparatus with the pipette devices to prevent contamination in introducing the sample fluid into the flow channel by replacing pipette tips each time that the fluid is changed over.

The sensor unit for use in the assay apparatus with the pipette devices includes a flow cell, the prism and a connection mechanism. The flow cell has the flow channel. The prism is overlaid with the thin film of metal. The sensor unit connects a flow cell with the prism by positioning the flow channel on the thin film. The thin film of the sensor unit also has the linker film. The pipette devices introduce the sample fluid such as ligand fluid and analyte fluid into the flow channel for assay.

However, it is likely in the assay apparatus with the pipette devices to create errors in measurement by incidentally shifting the sensor unit in loading or unloading the pipette devices on the flow channel. Such errors in the position of the sensor unit will change the position of the reflected light in the photo detector. Even if analysis according to a measuring signal and a reference signal is carried out, the error cannot be removed. In view of this, there is a suggestion in preventing offsetting of the sensor unit by pressurizing and holding the sensor unit downwards according to the direction of loading and unloading the pipette devices.

There is a problem in pressurizing and holding the sensor unit downwards by use of the connection mechanism and the flow cell. If external great force is exerted, the prism may be shift incidentally. Also force applied to the prism may change with time according to a change in elasticity of the connection mechanism or the flow cell. The change in the force may influence to correctness in the orientation of the prism.

SUMMARY OF THE INVENTION

In view of the foregoing problems, an object of the present invention is to provide a sensor unit for assay and a prism, in which a light path of photo detection can be prevented from offsetting in the course of assay.

In order to achieve the above and other objects and advantages of this invention, a sensor unit usable in an assay apparatus having an assay stage is provided. An optical block is supported on a stage surface of the assay stage, having a sensing surface positioned on an upper surface thereof, the sensing surface receiving illuminating light applied thereto to reflect the illuminating light. The assay apparatus receives the illuminating light reflected by the sensing surface, for measuring reaction of a sample. At least one engageable portion of a protruding or retreating shape is formed with the optical block, for keeping the optical block positioned on the stage surface by engagement with a retention mechanism of the assay apparatus.

The at least one engageable portion is two engageable portions disposed on first and second lateral faces of the optical block which are so positioned that the sensing surface is disposed between.

The optical block is in a prismatic shape defined by parallel shift of a predetermined quadrilateral in a block longitudinal direction, the quadrilateral having an upper side line and a lower side line shorter than the upper side line. The engageable portion is a ridge formed to project from a lower edge of the first and second lateral faces of the optical block extending in the block longitudinal direction.

In other words, the optical block is in a prismatic shape which is in an inverted trapezoidal form when viewed in a section. The engageable portion is a ridge formed to project from a lower edge of the first and second lateral faces of the optical block extending in a block longitudinal direction.

The ridge extends consecutively in the block longitudinal direction.

In one embodiment, the at least one engageable portion is plural engageable portions arranged in one line in the block longitudinal direction of the optical block.

Furthermore, a grip portion is formed at a first end of the optical block, and adapted to holding of the optical block.

The grip portion includes at least one projection formed to project from a lateral face of the first end and crosswise to the block longitudinal direction.

The grip portion includes a small width section, formed with a smaller width than the optical block, for projecting from the first end in the block longitudinal direction, the small width section having the at least one projection on a lateral face thereof.

The at least one projection and the small width section are defined by forming at least one grip channel in the optical block.

The grip portion is constituted by a small width portion, formed with a smaller width than the optical block and in a shape to increase the smaller width in a direction away from the optical block.

The optical block is a total reflection prism of which the upper surface is a total reflection surface.

The sensing surface is constituted by a layer of a thin film which is responsive to light applied by satisfying total reflection condition on the optical block, for attenuating intensity of reflected light thereof. The assay apparatus is an apparatus for assay in utilizing attenuated total reflection, and includes a light source for applying the illuminating light to the sensing surface by satisfying total reflection condition. A photo detector photoelectrically detects the illuminating light reflected by the sensing surface.

The retention mechanism includes at least one retention arm, movable between first and second positions, for engagement with a surface of the engageable portion for retention when in the first position, and for being away from the engageable portion when in the second position. A retention arm shifter shifts the retention arm between the first and second positions.

In one preferred embodiment, a total reflection prism usable in an optical apparatus having a stage is provided. A prism body is shaped prismatically or semi-cylindrically, supported on a stage surface of the stage, having a total reflection surface positioned on an upper surface thereof, the total reflection surface receiving illuminating light applied thereto by a light source of the optical apparatus to reflect the illuminating light totally. At least one engageable portion of a protruding or retreating shape is formed with the prism body, for keeping the prism body positioned on the stage surface by engagement with a retention mechanism of the optical apparatus.

The at least one engageable portion is two engageable portions disposed on first and second lateral faces of the prism body which are so positioned that the total reflection surface is disposed between.

BRIEF DESCRIPTION OF THE DRAWINGS

The above objects and advantages of the present invention will become more apparent from the following detailed description when read in connection with the accompanying drawings, in which.

DETAILED DESCRIPTION OF THE PREFERRED EMBODIMENT(S) OF THE PRESENT INVENTION

Figure 1:
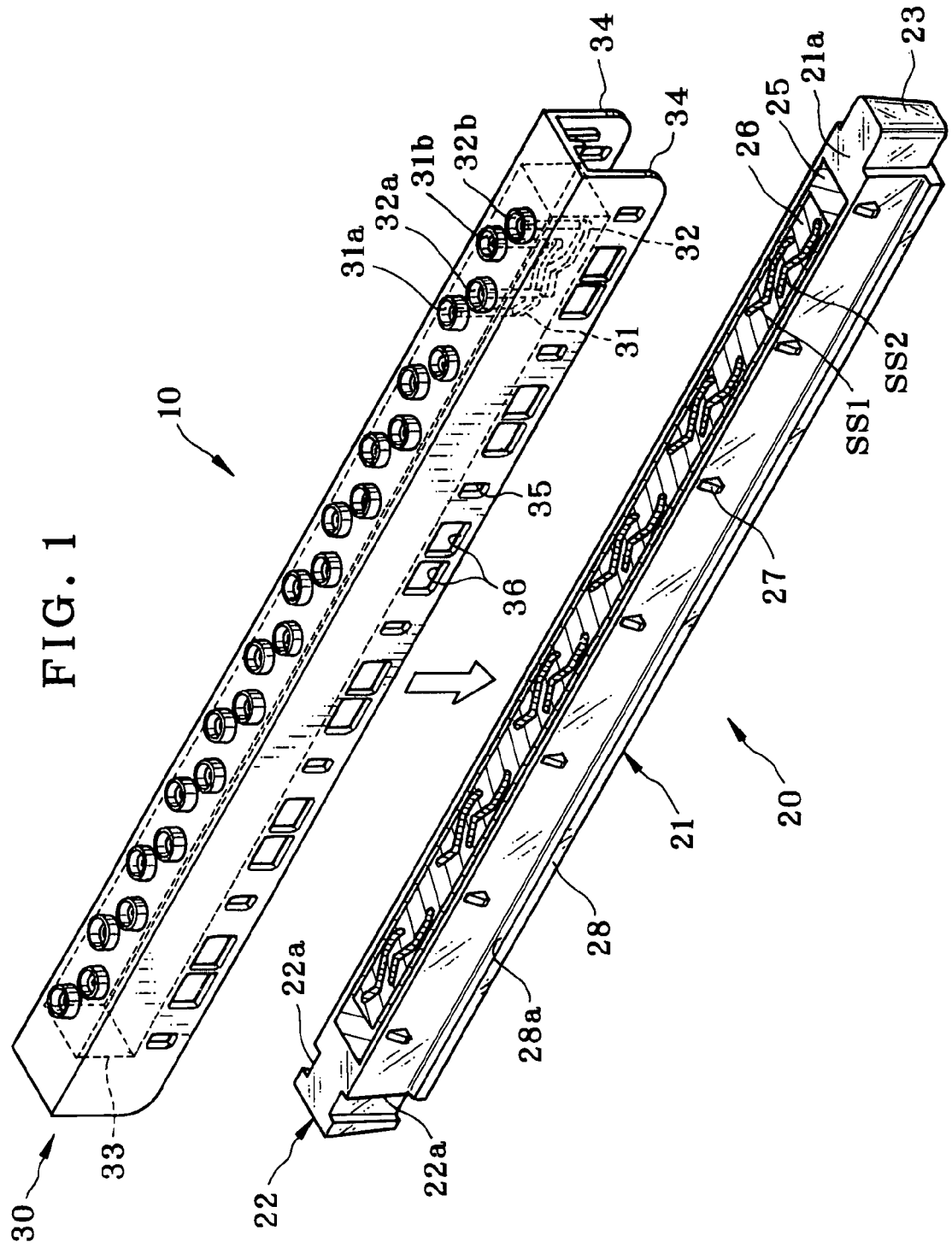
FIG. 1 is a perspective view illustrating a prism and a flow cell in a sensor unit.

In FIG. 1, a sensor unit 10 for surface plasmon resonance (SPR) assay is illustrated. The sensor unit 10 includes a total reflection prism 20 as optical block, and a flow cell 30. The prism 20 is a transparent dielectric optical block. The flow cell 30 is secured to the prism 20. A first flow channel 31 and a second flow channel 32 are formed in the flow cell 30. To assay samples, one combination including the flow channels 31 and 32 is used to measure the sample by use of the sensor unit 10. Six combinations of the flow channels 31 and 32 are formed in the flow cell 30 and arranged in its longitudinal direction. A single one of the sensor unit 10 can assay six samples at one time. Note that the number of the combinations of the flow channels 31 and 32 may be five or less, or may be seven or more.

The prism 20 includes a prism body 21, an end grip portion 22 at a first end, and an end projection 23. The prism body 21 is shaped in a form of a quadrilateral prism. The end projection 23 is formed at a second end opposite to the grip portion 22. The prism 20 is a single plastic piece inclusive of the prism body 21, the grip portion 22 and the end projection 23, and may be formed by extrusion or suitable forming methods. Various materials can be used for forming the prism 20, their examples including optical glasses, such as borosilicate crown (BK7) glass, barium crown (Bak4) glass, and the like; and optical plastic materials, such as polymethyl methacrylate (PMMA), polycarbonate (PC), amorphous polyolefin (APO) and the like.

A shape of the prism body 21 as viewed in a cross section is a trapezoid of which an upper side line is longer than a lower side line. An upper surface 21a of the prism body 21, as an metal/dielectric interface of the sensor unit, receives light condensed by the prism body 21. A thin film 25 of metal is overlaid on the prism body 21 to define the interface 21a, for generating surface plasmon resonance (SPR). The thin film 25 has a quadrilateral shape, is opposed to the flow channels 31 and 32 of the flow cell 30, and is formed by vapor deposition. Examples of materials for the thin film 25 are gold and silver. The thin film 25 is 50 nm thick. The thickness of the thin film 25 is determined suitably according to the substance for the thin film 25, a wavelength of illuminating light or the like.

A linker film 26 is overlaid on the thin film 25. The linker film 26 contains a reaction group for immobilizing the ligand. The ligand is immobilized on the thin film 25 by use of the linker film 26. Examples of materials of the linker film 26 include hydrogels, such as agarose, dextran, carrageenan, alginic acid, starch, and cellulose, and their derivatives, and also polyvinyl alcohol, polyacrylic acid, polyacrylamide, polyethylene glycol, and the like. A particular compound to form the linker film 26 is selected according to the type of the ligand for immobilization.

A typical example of the linker film 26 is carboxyl methyl dextran as a dextran derivative. At first, the thin film 25 is washed with water, ethanol or the like, and processed by surface processing with epichlorohydrin solution and the like. The prism 20 is set in an incubator/shaker, to incubate and shake the thin film 25 in contact with solution containing aqueous solution of dextran and sodium hydroxide at 25 degrees centigrade for 20 hours. Thus, the linker film 26 is produced. Note that washing and processing with bromoacetic acid may be added after processing the dextran. In FIG. 1, the size of the linker film 26 is slightly smaller the thin film 25. However, the linker film 26 can be formed on the entire surface of the thin film 25.

Plural connection claws 27 are formed on longitudinal lateral faces of the prism body 21 for coupling with the flow cell 30. Engageable ridges 28 as engageable portion are formed to project from the prism body 21 on its lower edges. An engageable surface 28a of the engageable ridges 28 extend horizontally and in parallel with the interface 21a of the thin film 25. The engageable ridges 28 are used for keeping the sensor unit 10 positioned in the assay apparatus.

The end grip portion 22 formed with the prism body 21 is in a form of a quadrilateral prism similar to the prism body 21. Grip recesses 22a as a small width section with grip projections are formed in lateral faces of the grip portion 22, which is in a T shape when viewed downwards from the upside. The grip portion 22 is manually grasped for holding the prism 20 and the sensor unit 10. Should a hand grasp or touch lateral faces of the sensor unit 10 extending in the longitudinal direction, dust is likely to stick to cause errors in the assay. If the upper face of the sensor unit 10 having the flow channels 31 and 32 is touched, dust is likely to enter the flow channels 31 and 32. In view of this, a user is allowed to touch the grip portion 22 and the end projection 23 with his or her hand.

The end projection 23 has a box shape at the end of the prism body 21, and manually grasped by a user to handle the sensor unit 10. Also, when a sensor holder (not shown) is used, the end projection 23 of the prism body 21 operates for positioning. A recess of the sensor holder for positioning the sensor unit 10 is engaged with the end projection 23 to keep the sensor unit 10 stable in the sensor holder.

The flow cell 30 includes a flow cell body 33 and two connection panels 34. The flow cell body 33 is a box shape having the flow channels 31 and 32. The connection panels 34 protrude down from the flow cell body 33 and extend longitudinally with the flow cell body 33. First orifices 31a and 32a of the flow channels 31 and 32 are open in an upper face of the flow cell body 33 for introduction of fluid. Second orifices 31b and 32b of the flow channels 31 and 32 are open in the flow cell body 33 for drawing and removal of the fluid. Each of the flow channels 31 and 32 is a conduit extending in a channel shape, and causes fluid to flow in contact with the linker film 26 of the prism 20 after introduction through the first orifices 31a and 32a. The fluid is removed through the second orifices 31b and 32b.

The flow channels 31 and 32 are arranged in two lines that are so disposed that the center line of the flow cell 30 extends between those. The flow channels 31 and 32 extend in parallel with the longitudinal direction of the flow cell 30. The second flow channel 32 is offset from the first flow channel 31 when viewed vertically to the longitudinal direction. A diameter of the flow channels 31 and 32 is approximately 1 mm. An interval between the first and second orifices 31a and 31b and between the first and second orifices 32a and 32b is approximately 10 mm.

Connection holes 35 are formed in the connection panels 34 and associated with the connection claws 27 of the prism 20. The connection claws 27 are engaged with the connection holes 35 to retain the flow cell 30 on the prism 20 in contact of a lower surface of the flow cell body 33 on an upper surface of the prism 20. An open lower face of the flow channels 31 and 32 is closed by the upper surface of the prism 20. The number of the connection claws 27 and of the connection panels 34 is seven (7) in the block longitudinal direction. The connection claws 27 and the connection panels 34 are positioned at ends of the flow channels 31 and 32. A firm state of the contact of the flow channels 31 and 32 is kept equal without a specific difference.

When the ligand fluid containing the ligand and fluid medium is sent to the flow channels 31 and 32, the ligand is immobilized only on portions of a surface of the linker film 26 positioned at the flow channels 31 and 32. These portions constitute sensing surfaces where interaction between the ligand and analyte occurs. A portion of the linker film 26 positioned at the first flow channel 31 is referred to as a first sensing surface SS1. A portion of the linker film 26 positioned at the second flow channel 32 is referred to as a second sensing surface SS2.

Openings 36 are formed in the connection panels 34 for partially uncovering lateral faces of the prism body 21. The number of the openings 36 is 12 according to the embodiment in view of the plural combinations of the flow channels 31 and 32. The openings 36 constitute paths of light for application to the sensing surfaces SS1 and SS2. After the total reflection, light from the sensing surfaces SS1 and SS2 passes some of the openings 36 for exit.

The flow cell 30, similar to the prism 20, is a single plastic piece formed by extrusion or the like, and is inclusive of the flow cell body 33 and the connection panels 34. An example of material for the flow cell 30 is polypropylene or other crystalline polyolefin. Furthermore, the flow channels 31 and 32 should be fluid tight while the flow cell 30 is secured to the prism 20. To this end, a flexible part or layer as sealant is preferably formed on edges of lower open portions of the flow channels 31 and 32 in a deformable manner between a lower face of the flow cell body 33 and the thin film 25 of the prism body 21. Note that the use of adhesive agent for the flexible part may cause a problem because the adhesive agent as foreign material may enter the flow channels 31 and 32. To add a flexible part, it is preferable to use two color molding, namely double molding to mold the flexible part together with the flow cell body 33 of the flow cell 30. A preferable material for the flexible part is amorphous polyolefin elastomer or other material with small non-specific adsorption to prevent non-specific adsorption.

The prism 20 as a molded piece is shaped for being drawn away upwards from a mold because an upper surface with the sensing surface SS1 and SS2 and a lower surface for placement on the assay apparatus should be flat and smooth. Thus, draft with a draft angle of 2-3 degrees is formed on end faces of the prism 20 except for the lateral faces of the prism body 21 which operates optically for entrance and exit of illuminating light.

The prism 20 after being molded is inspected according a predetermined size. If lateral faces are inclined in a manner different from the predetermined size, the prism 20 is difficult to set in combination with a measuring instrument, to make it difficult to measure the size. This problem is particularly serious in the longitudinal size. Therefore, in FIG. 2A, a reference flat surface 29a is formed on an upper end of a draft surface 29 with an inclination. The reference flat surface 29a is disposed on one of lateral surfaces of the prism body 21 having the end grip portion 22, and extends vertically to the interface 21a of the thin film 25 and vertically to the block longitudinal direction.

Thus, the measuring instrument can be positioned easily on the prism 20, of which a length in the longitudinal direction can be exactly measured by positioning of the reference flat surface 29a as a reference of inspection. Note that the form of the reference flat surface 29a is local absence of the draft. In spite of importance of draft for good moldability, the shape of the reference flat surface 29a is consistent to keeping good moldability, and is free from likeliness of unwanted crack, deformation and the like.

Figure 2A:
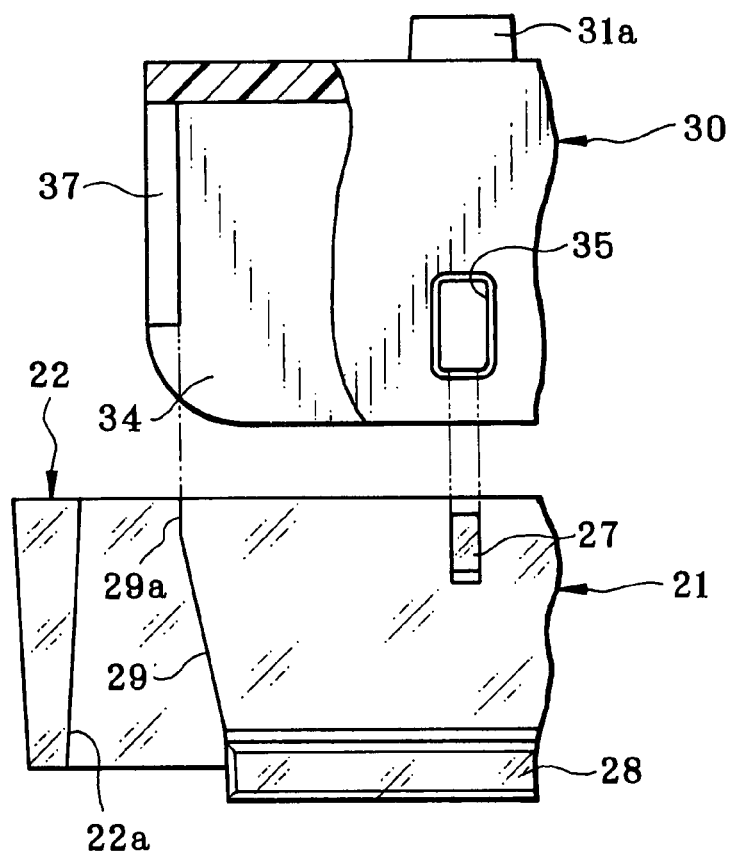
FIG. 2A is a side elevation, partially cutaway illustrating the sensor unit of FIG. 1 with a reference flat surface.
Figure 2B:
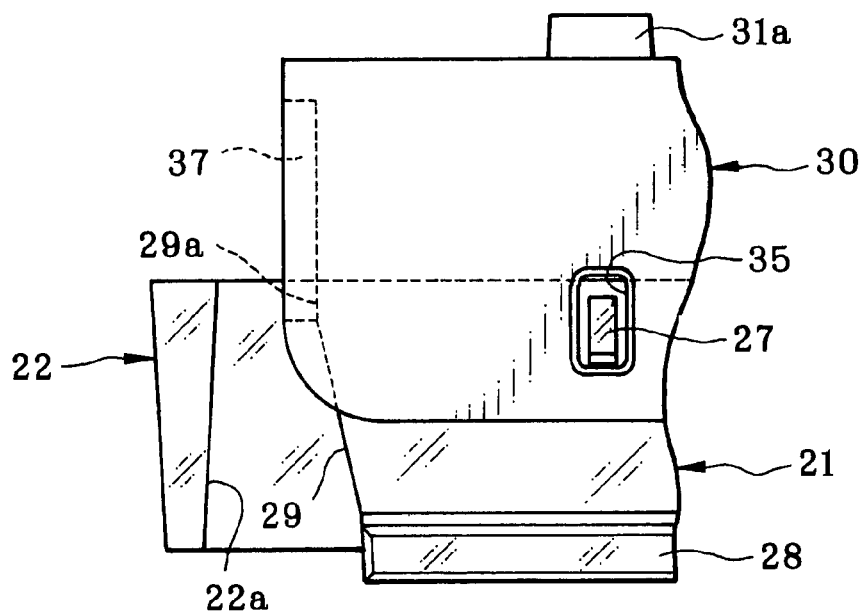
FIG. 2B is a side elevation, partially cutaway illustrating the same as FIG. 2A but in a connected state.

In FIG. 2A, a ridge 37 is formed inside the connection panels 34 of the flow cell 30 and extends straight. In FIG. 2B, the ridge 37 contacts the reference flat surface 29a to position the flow cell 30 longitudinally when the flow cell 30 is secured to the prism 20 by engaging the connection claws 27 with the connection holes 35.

Note that an RFID tag (radio frequency identification tag) as a non-contact IC memory may be used with and secured to any one element in the sensor unit 10 such as the prism 20 and the flow cell 30. An ID number for the sensor unit 10 is stored in the RFID tag of the read only type. The ID number is read out at each time before operation of one of sequential processes, so the sensor unit 10 can be identified. It is possible to prevent failure or errors in simultaneous immobilization and assay of plural sensor units, such as erroneous introduction of analyte fluid, misreading of results of measurement. Also, the RFID tag may be a writeable type. Information can be written to the RFID tag in sequential processes, such as types of immobilized ligand, date and time of immobilization, types of analytes used in the reaction, and the like.

Figure 3:
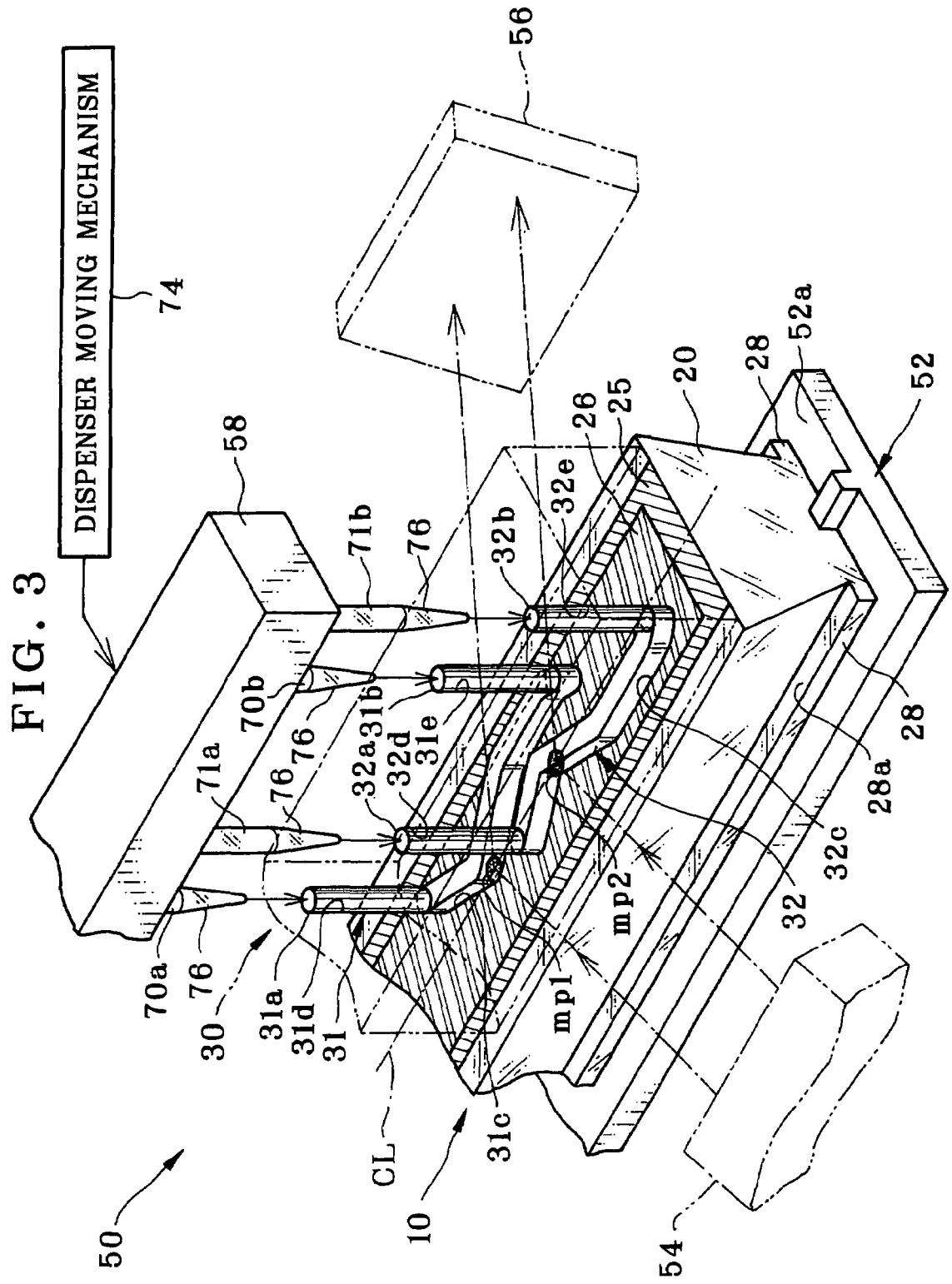
FIG. 3 is a perspective view illustrating an assay apparatus.

In FIG. 3, a surface plasmon resonance (SPR) assay apparatus 50 is schematically illustrated as optical apparatus. The assay apparatus 50 includes an assay stage 52, a light source 54, a photo detector 56, and a dispensing head or pipette head 58. A stage surface 52a is defined on the assay stage 52 for placement of the sensor unit 10. The light source 54 emits illuminating light for application to the sensor unit 10 by satisfying a total reflection condition. The photo detector 56 receives light reflected by the sensor unit 10 in the total reflection, and photoelectrically converts the light into an electric signal as SPR signal. The dispensing head 58 sends liquid to the sensor unit 10. A controller (not shown) of the assay apparatus 50 controls those elements systematically.

In FIG. 3, the first flow channel 31 includes a passageway 31c, a first conduit zone 31d, and a second conduit zone 31e. The passageway 31c is open in a lower face of the flow cell 30. The first conduit zone 31d extends from a first end of the passageway 31c, comes through the flow cell 30 and has the first orifice 31a at its upper end. The second conduit zone 31e extends from a second end of the passageway 31c, comes through the flow cell 30 and has the second orifice 31b at its upper end. Similarly, the second flow channel 32 includes a passageway 32c, a first conduit zone 32d, and a second conduit zone 32e.

When the flow cell 30 is fitted on the prism 20, the passageways 31c and 32c of the flow channels 31 and 32 are covered and closed hermetically by the thin film 25 of the prism body 21. As described heretofore, the fluid introduced in the flow channels 31 and 32 flows in contact with the linker film 26. Each of the passageways 31c and 32c are flexed in the S shape with a point that lies on the center line CL of the thin film 25 of the prism body 21.

The light source 54 applies illuminating light of various incident angles to each of the sensing surfaces SS1 and SS2 at the same time by satisfying a total reflection condition. The position and angle of the light source 54 are predetermined so that light condensed at the interface 21a of the thin film 25 upon entry in the prism 20 impinges portions of the sensing surfaces SS1 and SS2 passing through the center line CL.

A refractive index of the sensing surfaces SS1 and SS2 changes upon flow of fluid through the flow channels 31 and 32, because of immobilization of ligand on the linker film 26, interaction between the ligand and analyte and the like. In the assay apparatus 50, light from the light source 54 is condensed at a point that is located on the central line CL of the sensing surfaces SS1 and SS2. The photo detector 56 receives the reflected light to detect changes in the refractive index. A portion of the first sensing surface SS1 in condensation of light from the light source 54 is referred to as a first measuring point mp1. A portion of the second sensing surface SS2 in condensation of light from the light source 54 is referred to as a second measuring point mp2.

The light source 54 includes a light source device (not shown) and optical system having a condensing lens, diffuser, polarizer and the like. Examples of the light source device include a light emitting diode (LED), laser diode (LD), super luminescent diode (SLD), and other light emitting element. The light source 54 illuminates the measuring points mp1 and mp2. To this end, two light source devices are arranged and used. Otherwise, a single light source device is used with an additional prism for splitting light from the light source device into two paths.

The diffusing plate diffuses light from the light source, and suppresses onset of irregularity in the light amount. The polarizer allows only p-polarized light to pass, the p-polarized light creating the surface plasmon resonance. Note that no polarizer is required if directions of rays emitted by the light source, for example an LD, are originally equal. However, a diffusing plate may be combined with the light source of a type of which directions of emitted rays are kept equal. Directions of rays in polarization are changed to an unequal state by the passage through the diffusing plate. For this structure, the polarizer can be utilized to set equal the directions of the rays. The light obtained after the diffusion and polarization is condensed by a condensing lens, and directed to the prism 20. It is possible to travel rays with various angles of incidence toward the measuring points mp1 and mp2 without irregularity in the intensity.

An example of the photo detector 56 is a CCD area sensor or an array of photo diodes. Light, upon entry into the prism body 21 through one lateral face, is condensed on the interface 21a of the thin film 25 on the prism body 21 as a back surface of the thin film 25, and totally reflected by the prism body 21 to travel and exit through a second lateral face. Rays of light are incident upon the interface 21a at various angles. The light is reflected by the interface 21a at various angles of reflection according to the angles of the incidence. The photo detector 56 receives reflected light of plural angles, converts the same photoelectrically, to output an SPR signal at a level of the light intensity. The photo detector 56 receives both reflected light from the first measuring point mp1 and reflected light from the second measuring point mp2, to output SPR signals. Measurement of two signal channels is possible in the light source 54 and the photo detector 56.

If a CCD area sensor is used as the photo detector 56, reflected light of the dual channels received at the same time can be recognized as an SPR signal for the first measuring point mp1 and an SPR signal for the second measuring point mp2 by the image processing. However, such a method according to the image processing might be too difficult. Alternatively, signals of the signal channels can be received by differentiating the time sequence for a very small period of time of the incidence between the first and second measuring points mp1 and mp2. An example of differentiating the time sequence is a use of a disk disposed on a light path of the light source 54 and having two holes positioned at 180 degrees of a rotational angle. The disk is rotated to shift the time sequence between the signal channels. The holes are disposed at a difference of the radius from the rotational center in association with the interval between the first and second measuring points mp1 and mp2. When a first one of the holes enters the light path, illuminating light travels to the first measuring point mp1. When a second one of the holes enters the light path, the light travels to the second measuring point mp2. Thus, the time sequence of entry to the signal channels is differentiated. Note that the photo detector 56 as single device receives light from the measuring points mp1 and mp2. However, two detectors may be used separately for each of the measuring points mp1 and mp2.

The assay apparatus 50 has six combinations of the light source 54 and the photo detector 56 although those are depicted in a simplified manner in FIG. 3. The sensing surfaces SS1 and SS2 of six combinations in the sensor unit 10 are assayed simultaneously. Note that a splitting device may be used to split light from a single light source device into 12 paths for the purpose of applying light simultaneously to the sensing surfaces SS1 and SS2 for assay. Also, a moving mechanism may be added.

One combination of the light source 54 and the photo detector 56 is used. The moving mechanism moves the sensor unit 10 in the longitudinal direction to shift the sensing surfaces SS1 and SS2 into a light path of the illuminating light, to assay combinations of the sensing surfaces SS1 and SS2 intermittently after one another.

In the dispensing head 58 are arranged pipette devices 70a and 70b and pipette devices 71a and 71b. The pipette devices 70a and 70b access to the first and second orifices 31a and 31b of the first flow channel 31. The pipette devices 71a and 71b access to the first and second orifices 32a and 32b of the second flow channel 32. A syringe pump is connected with each of the pipette devices 70a, 70b, 71a and 71b, and is driven to dispense and aspirate fluid. The pipette devices 70a, 70b, 71a and 71b, although simplified in the drawing, are disposed for each of the flow channels 31 and 32 in a manner similar to the light source 54 and the photo detector 56.

A dispenser moving mechanism 74 is associated with the dispensing head 58. The dispenser moving mechanism 74 is a moving mechanism and may include a conveyor belt, pulleys, a carriage and a motor. A controller (not shown) controls the dispenser moving mechanism 74 to move the dispensing head 58 in three dimensional manner, namely in a direction between the front and rear, a direction between the right and left sides, and a vertical direction.

The pipette devices 70a, 70b, 71a and 71b are formed in the dispensing head 58 to protrude in a tubular shape. Pipette tips 76 are disposed as ends of the pipette devices 70a, 70b, 71a and 71b, and are secured thereto in a removable manner. The pipette tips 76 are detipped for renewal after each time of fluid introduction so as to prevent mixture and contamination of plural liquids in the pipette tips 76 in direct contact with flowing liquid through the pipette devices 70a, 70b, 71a and 71b. A pipette tip storage (not shown) is incorporated in the assay apparatus 50 and stores the pipette tips 76. The dispenser moving mechanism 74 causes the dispensing head 58 to access to the pipette tip storage for the purpose of replacing the pipette tips 76.

A fluid reservoir or multi well plate (not shown) is incorporated in the assay apparatus 50, and stores various fluids for introduction to the flow channels 31 and 32, for example, ligand fluid, analyte fluid, washing liquid, buffer liquid and the like. The dispenser moving mechanism 74 moves the dispensing head 58 to access to plural positions which are the fluid reservoir or multi well plate, and the sensor unit 10 set on the assay stage 52.

To introduce fluid to the flow channels 31 and 32 with the dispensing head 58, at first the dispenser moving mechanism 74 is driven for the dispensing head 58 to access to the fluid storage. The dispensing head 58 causes the pipette devices 70a and 71a to aspirate fluid before insertion in the first orifices 31a and 32a. Then the dispenser moving mechanism 74 is driven for the dispensing head 58 to access to the sensor unit 10. The dispensing head 58 sets the pipette devices 70a, 70b, 71a and 71b at the first orifices 31a and 32a and the second orifices 31b and 32b. Fluid is dispensed by the dispensing head 58 through the pipette devices 70a and 71a. Also, the pipette devices 70b and 71b aspirate and draw fluid from the flow channels 31 and 32, for example air or liquid previously introduced. Thus, the fluid in the flow channels 31 and 32 is replaced.

Figure 4:
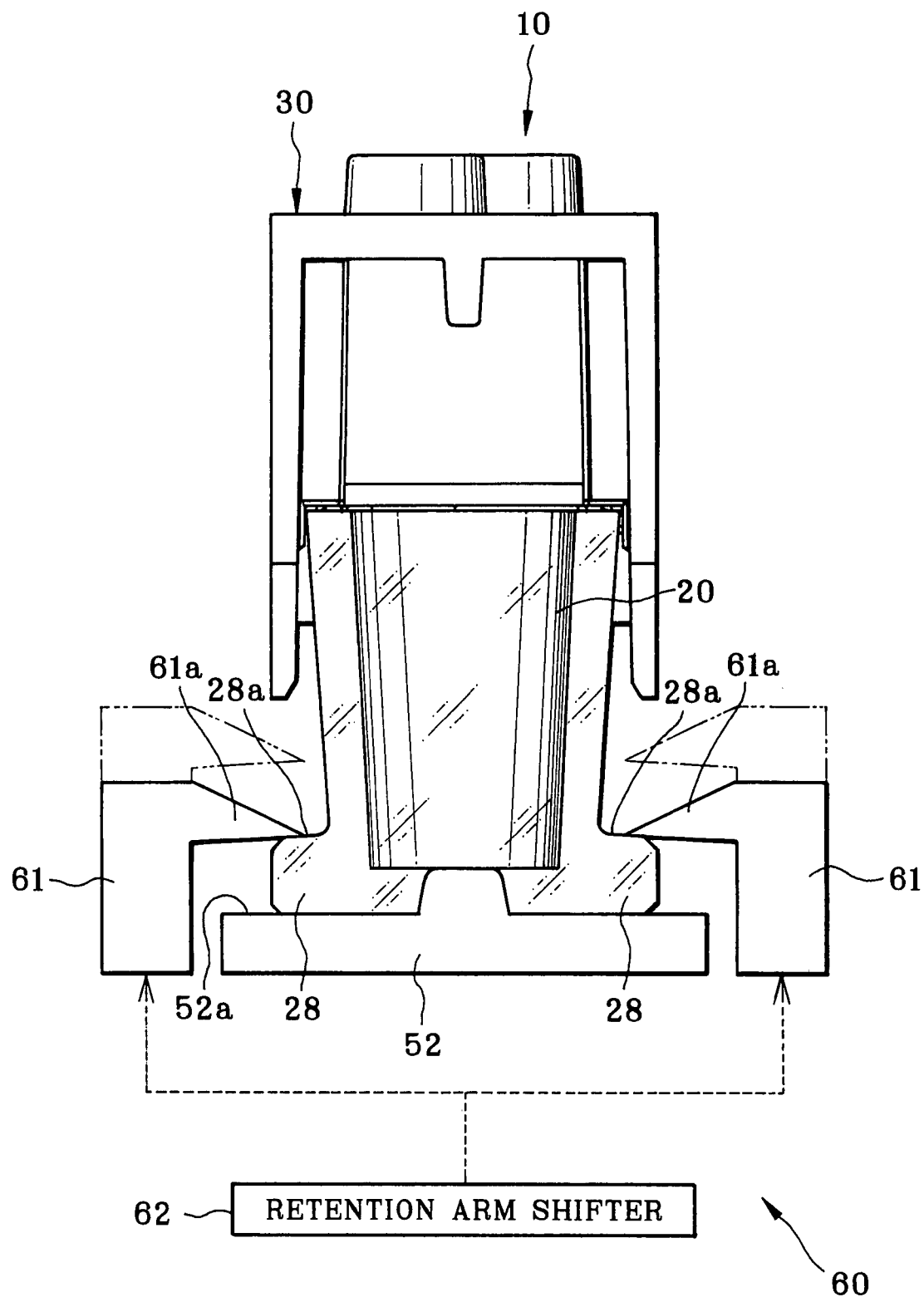
FIG. 4 is a side elevation illustrating a retention mechanism.

In FIG. 4, the assay apparatus 50 has a retention mechanism 60 including retention arms 61, and a retention arm shifter 62 for clamping. The retention arms 61 are opposed to one another, and are so disposed that the sensor unit 10 on the assay stage 52 lies between those. The retention arm shifter 62 shifts the retention arms 61 between a retaining position and a releasing position. The retention arms 61, when in the retaining position indicated by the solid line, keep the sensor unit 10 positioned on the stage surface 52a of the assay stage 52, and when in the releasing position indicated by the phantom line, release the sensor unit 10 from the retention.

Clamping claws 61a are formed on the retention arms 61. When the retention arms 61 shift to the retaining position, the clamping claws 61a are engaged with the engageable surface 28a to keep the prism body 21 in contact with the stage surface 52a by clamping. The retention arm shifter 62 may have a mechanical structure including gears, a motor and other well-known elements, and responsive to command signals from the controller, shifts the retention arms 61 between a retaining position and a releasing position. When the sensor unit 10 is placed on the assay position of FIG. 3 on the assay stage 52 where the illuminating light of the light source 54 travels to the measuring points mp1 and mp2, the controller causes the retention arm shifter 62 to shift the retention arms 61 to the retaining position to keep the sensor unit 10 positioned. Note that any suitable structure may be used in the retention arm shifter 62. For example, a manually operable lever may be a shifter for shifting the retention arms 61.

The assay operation of the assay apparatus 50 includes a sample immobilizing flow step, assay step, and data analysis step. In the sample immobilizing flow, ligand fluid is introduced to flow on the linker film 26 for immobilizing ligand. In the assay, reaction is caused between the ligand and analyte to obtain SPR signal. In the data analysis, the SPR signal is evaluated to analyze characteristics of samples.

In the sample immobilizing flow, the ligand fluid is introduced to the first flow channel 31 by the dispensing head 58. The ligand fluid is kept in the first flow channel 31 and in contact with the sensing surface SS1, and is removed after completing the immobilization. In general, approximately one (1) hour is taken for the immobilization of the ligand. The sensor unit 10 is left to stand with stabilized environment, for example temperature. The ligand from the ligand fluid becomes immobilized on the sensing surface SS1.

Until the immobilization, the ligand fluid in the first flow channel 31 may be left to stand in a stationary state. However, the ligand fluid can be preferably stirred or turbulently flowed by alternately driving the pipette devices 70*a* and 70*b* between dispensation and aspiration, for ensured fluidity in the first flow channel 31. The stirring or turbulent flow can promote binding of the ligand with the linker film 26, to raise an immobilized amount of the ligand. Also, it is possible to wash the inside of the first flow channel 31 or activate the linker film 26 before introduction of the ligand fluid into the first flow channel 31.

For the assay, the analyte fluid is introduced to each of the flow channels 31 and 32 upon starting reading of SPR signals on the photo detector 56 with the light source 54. The light source 54 applies illuminating light to the first and second measuring points mp1 and mp2. The photo detector 56 obtains SPR signals from reflected light of the first and second measuring points mp1 and mp2. As the ligand is immobilized only on the first sensing surface SS1 in the sample immobilization, a measuring signal or SPR signal is obtained from the first measuring point mp1 to represent interaction between the ligand and analyte. In contrast, no ligand is immobilized on the second sensing surface SS2. A reference signal or SPR signal is obtained from the second measuring point mp2 to represent only flow of analyte.

For the assay in the assay apparatus, liquid buffer is introduced into the flow channels 31 and 32 and caused to flow before and after introducing analyte. Reading of data in the photo detector 56 with the light source 54 starts before initially introducing the liquid buffer, and is continued until the completion of introduction of the liquid buffer at the second time. It is possible not only to detect the reference level but to assay interaction or reaction between the analyte and the ligand, and to measure a signal until dissociation between the analyte and ligand. Various liquids are available for use as the liquid buffer for assay, and solvent or diluent for samples. Examples of the liquids include buffer liquids, or physiological saline water and other aqueous solutions of physiological salts, and pure water. To facilitate dissolving of the analyte, dimethyl sulfo-oxide (DMSO) can be added to the physiological saline water.

For the data analysis, a controller (not shown) operates. At first, arithmetic processing of the measuring signal and the reference signal is carried out, for example determination of a finite difference or a ratio between those. The reference signal represents a change in the reference level. A finite difference between the signals obtained simultaneously so as to cancel electric noise caused externally by such factors as specific differences of the sensor unit 10, changes in the temperature of the fluid and the like. After the correction, the controller analyzes characteristics of samples or the like by evaluating changes in the resonance angle according to the corrected signal. The light source 54 and the photo detector 56 in the assay apparatus 50 obtain changes in the refractive index on the sensing surfaces SS1 and SS2 as changes in the SPR resonance angle, to measure interaction between the ligand and analyte.

Figure 5:
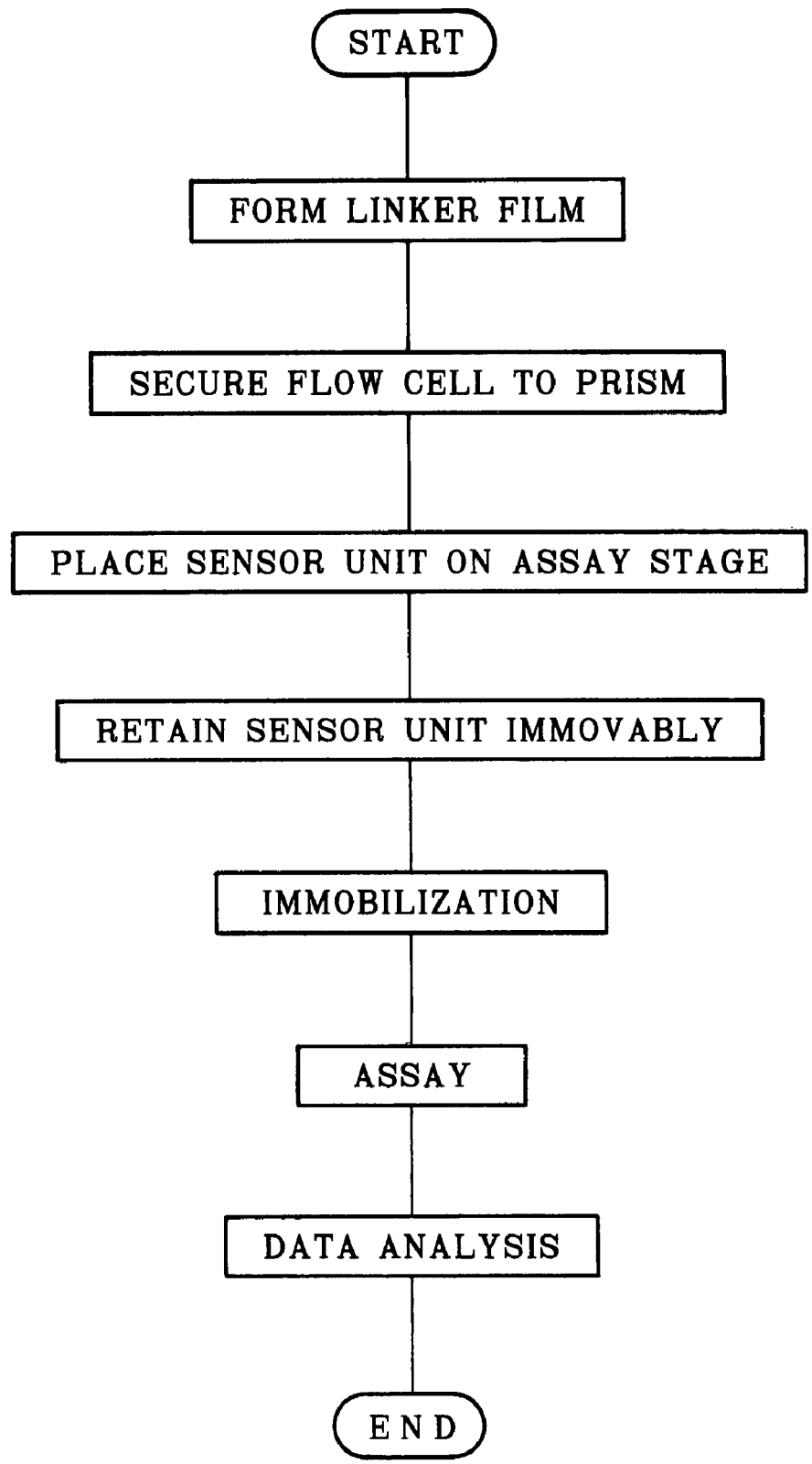
FIG. 5 is a flow chart illustrating a process of assay.

The operation of the sensor unit 10 and the assay apparatus 50 is described by referring to the flow of FIG. 5. To assay the interaction between the ligand and analyte, the linker film 26 is produced according to the type of the ligand. The prism 20 being unused is preserved and stored in a prism holder specified for the prism 20. To form the linker film 26, the end grip portion 22 and the end projection 23 at the ends of the prism body 21 are picked up by a user manually to remove the prism 20 from the prism holder. The prism 20 is set in an incubator/shaker. The prism 20 is subjected to incubation and shaking in the condition of the temperature and time described above, to form the linker film 26 on the thin film 25.

The prism 20 after forming the linker film 26 is removed from the incubator/shaker by grasping and raising the end grip portion 22 and the end projection 23. The use of the grip portion 22 and the end projection 23 makes it possible in moving the prism 20 to prevent sticking of dust, fingerprints or the like to lateral faces of the prism 20, the thin film 25, and the linker film 26. Also, the grip recesses 22*a* are formed in the grip portion 22 so that the prism 20 can be grasped stably by easy handling of a hand of a user.

After forming the linker film 26, the flow cell 30 is mounted on the prism 20. The ridge 37 is caused to contact the reference flat surface 29*a* near to the end face of the prism body 21. See FIG. 2. During the contact, the connection holes 35 are engaged with the connection claws 27 to secure the flow cell 30 to the prism 20. As described heretofore, the reference flat surface 29*a* is used as a reference of size inspection of the prism 20, so a longitudinal size of the prism 20 can be measured easily and exactly. Consequently, the flow channels 31 and 32 can be positioned accurately in the longitudinal direction by the contact of the ridge 37 on the reference flat surface 29*a*.

The sensor unit 10 obtained by setting the flow cell 30 on the prism 20 is placed on the stage surface 52*a* of the assay stage 52. The sensor unit 10 is set in the assay position of FIG. 3 where the illuminating light of the light source 54 becomes incident upon the measuring points mp1 and mp2. Then the retention arm shifter 62 of the retention mechanism 60 is driven to shift the retention arms 61 from the releasing position to the retaining position. See FIG. 4. In the retention arms 61 in the retaining position, the clamping claws 61*a* are engaged with the engageable surface 28*a*. The sensor unit 10 is kept firmly positioned on the assay stage 52 by pressing the prism body 21 on the stage surface 52*a*.

Consequently, the offsetting of the prism 20 in the position can be reliably prevented even when external force is applied to the sensor unit 10 upon movement of the pipette devices 70*a*, 70*b*, 71*a* and 71*b*. Note that the flow cell 30 can be pressed downwards additionally by an upper mechanism in combination with the retention arms 61 for the prism 20. This is effective in holding the sensor unit 10 more firmly.

The assay apparatus 50 of which the sensor unit 10 is positioned on the assay stage 52 subjects the sensor unit 10 for sample immobilization, assay and data analysis, and acquire data of samples, for example characteristics. The end grip portion 22 with the grip recesses 22*a* is formed at the end of the prism body 21 in the sensor unit 10, so that the sensor unit 10 can be grasped in moving the sensor unit 10 or the prism 20. Also, the reference flat surface 29*a* is formed with the prism 20, so as to inspect the size of the prism 20 easily and correctly by keeping good moldability without drop. Also, positions of the flow channels 31 and 32 can be determined exactly. Also, the entirety of the prism 20 can be retained by forming the engageable ridges 28 on a lower side of the prism body 21 to extend in the longitudinal direction of the prism body 21. This is effective in reliably preventing offsetting of the prism 20.

In the embodiment, a hand of a user moves the sensor unit 10 and the prism 20 by manually grasping those. However, a feeder or other moving mechanism well known in the art may be used for automated moving to an incubator/shaker or the assay apparatus 50. It is preferable in the moving mechanism to use a claw, arm, hook or the like for engagement with the grip recesses 22*a* in the end grip portion 22 for ensured holding of the prism 20. The automated moving can be stable.

In the embodiment, the end grip portion 22 is formed only at one end of the prism body 21. However, each of two ends of the prism body 21 may be provided with the grip portion 22.

The single structure of the grip portion 22, however, is preferable on the prism body 21 in view of the plural assay positions arranged in the block longitudinal direction in FIG. 1. If an error occurs in the direction of the sensor unit 10 set in the assay apparatus 50, results of the assay will be misread according to the reverse direction of the assay positions. However, as the grip portion 22 is single, the prism 20 is asymmetric, to facilitate recognition of the orientation of the sensor unit 10 to users. Errors in directing the sensor unit 10 can be prevented.

Note that the end grip portion 22, which is in the box shape according to the embodiment, may be formed in any shape, for example, a polygonal prism, a cylinder or the like. Despite the two of the grip recesses 22a, only a single channel may be formed in any of the lateral surfaces. Also, the grip recesses 22a can be formed in any of faces of the grip portion 22, for example an upper face or lower face. Also, the grip recesses 22a may be four channels arranged to extend the periphery of the grip portion 22 in a quadrilateral form.

Figure 6A:
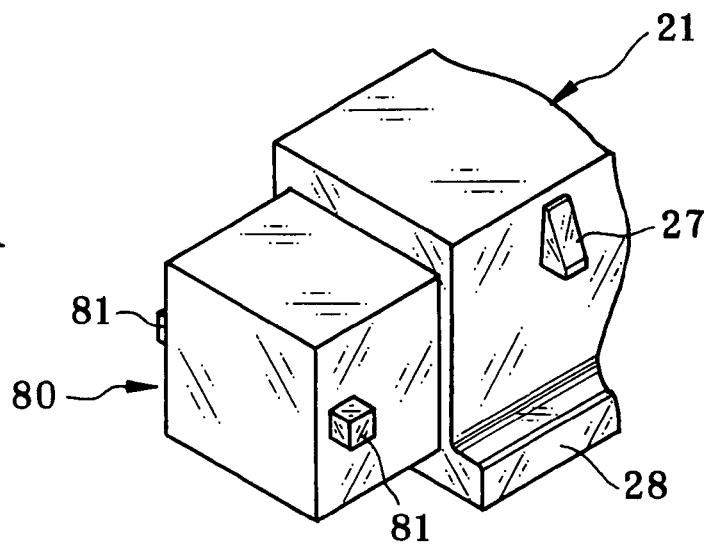
FIG. 6A is a perspective view, partially cutaway illustrating one preferred grip portion.
Figure 6B:
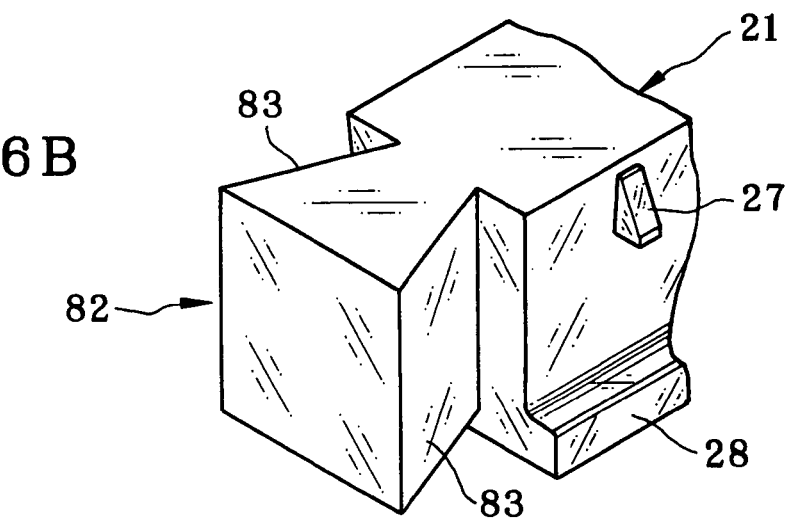
FIG. 6B is a perspective view, partially cutaway illustrating a preferred grip portion of a triangular shape.
Figure 6C:
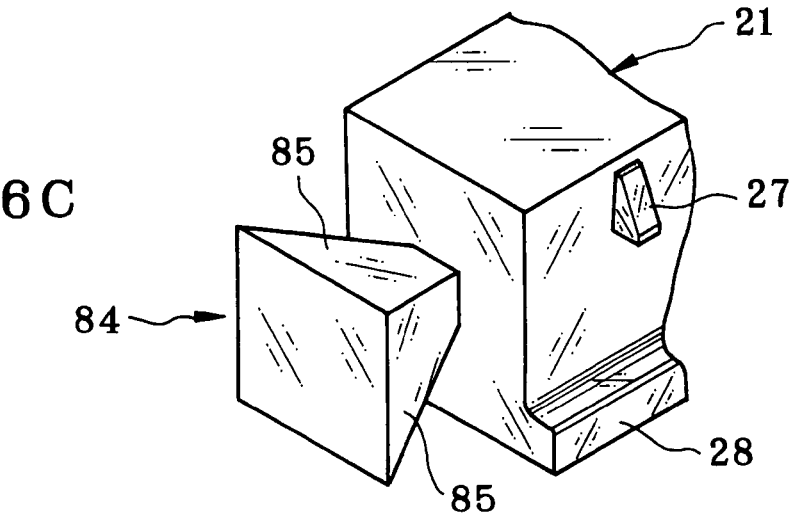
FIG. 6C is a perspective view, partially cutaway illustrating a preferred grip portion with a pyramidal surface.

In FIG. 6A, another preferred end grip portion 80 is illustrated as a small width section at a first end. Grip projections 81 are formed on the grip portion 80. In FIG. 6B, one preferred grip portion 82 is formed at a first end. An inclined surface 83 on a small width portion being the grip portion 82 is inclined in a form to decrease an area of a section toward the prism body 21. In FIG. 6C, a preferred grip portion 84 at a first end is illustrated. An inclined surface 85 for a small width portion is a pyramidal surface about the grip portion 84. Also, a conical surface may be used in place of the pyramidal surface. Accordingly, the prism 20 can be stably held by manual handling owing to the structure with the grip projections 81, the inclined surface 83 or the inclined surface 85.

In the embodiment, the prism body 21 is one molded piece including the end grip portion 22. However, the grip portion 22 may be an initial separate piece, and can be secured to the prism body 21 by adhesion, fastening with a screw, and other suitable methods.

In the above embodiment, the reference flat surface 29a is formed on one of two end faces of the prism body 21. However, the reference flat surface 29a can be formed on each of the two end faces of the prism body 21. Furthermore, it is possible to form a reference flat surface in a portion of a lateral surface of the prism body 21 extending longitudinally. The reference flat surface can be used for inspection of the size of the prism 20 in the block width direction, and for positioning the flow channels 31 and 32 in the block width direction.

In the above embodiment, the reference flat surface 29a is located at an upper end of the face of the prism body 21. However, the reference flat surface 29a may be located in any position of the prism body 21, for example a lower end, a middle point or the like. However, the location of the reference flat surface 29a at the upper end is particularly preferable in consideration of great ease in positioning of a measuring instrument for size inspection and positioning of the flow cell 30 in comparison with the location at a lower end, a middle point or the like.

Figure 7:
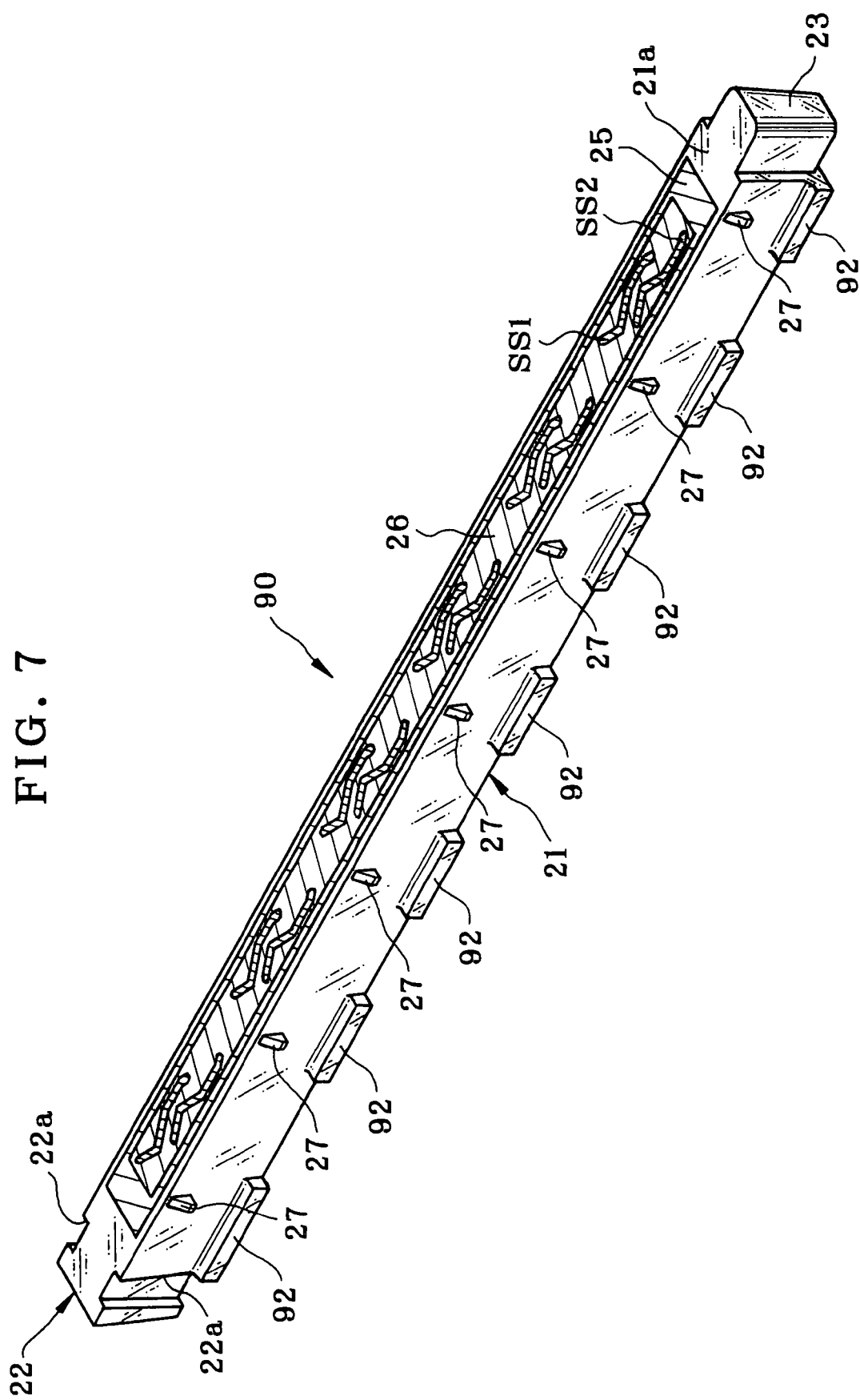
FIG. 7 is a perspective view illustrating one preferred embodiment having plural ridges in a line.

In FIG. 7, one preferred total reflection prism 90 as optical block is illustrated. Unlike the engageable ridges 28 of the above embodiment, a plurality of engageable ridges 92 as engageable portion are formed on the prism body 21 in a split form, and arranged in parallel with the longitudinal direction of the prism body 21.

Figure 8:
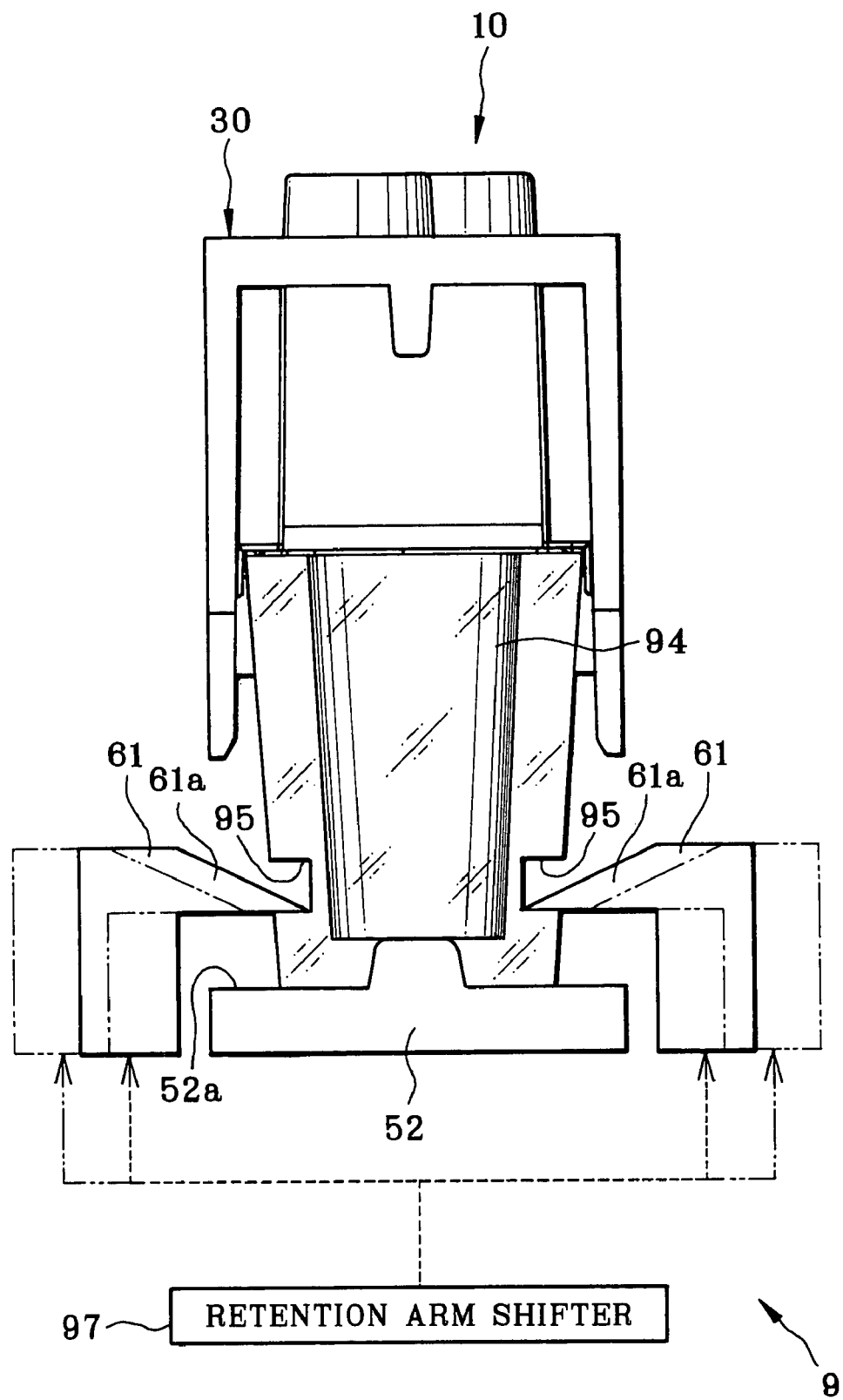
FIG. 8 is a side elevation illustrating another preferred embodiment having engageable channels.

In the above embodiment, the engageable ridges 28 and 92 are protrusions. Another preferred embodiment is illustrated in FIG. 8 and includes engageable channels in place of the ridges. In FIG. 8, a total reflection prism 94 as optical block includes engageable channels 95 as engageable portion formed in lateral faces. A retention mechanism 96 is combined with the engageable channels 95. A retention arm shifter 97 for clamping with the retention mechanism 96 is constructed to slide the retention arms 61 between a retaining position and a releasing position. The retention arms 61 in the retaining position enter the clamping claws 61a in the engageable channels 95 for engagement. The prism 94 is placed and kept positioned on the stage surface 52a. Similar effects can be obtained with the engageable channels 95 further to the above embodiment.

In the embodiment, plural combinations of the flow channels 31 and 32 are arranged to define two arrays of flow channels. However, a single array of flow channels may be formed to include the flow channels 31 and 32. However, the two arrays are still preferable, because the single array of the flow channels 31 and 32 is likely to enlarge the size of the sensor unit 10, and may create an obstacle to raising throughput of the assay.

Furthermore, a local portion of the linker film 26 on the sensing surface may be deactivated by processing. According to the photo detection, an SPR signal from the deactivated portion may be used as a reference signal. This is effective because two signals can be obtained for assay by the single flow channel. However, this is a simplified structure with a remaining problem in that a difference occurs in the surface characteristics of the linker film 26 between the deactivated portion and an original portion without the deactivation. An error is likely to occur in the measurement due to a difference in the amount of the non-specific adsorption between the two portions.

The separate use of the flow channels 31 and 32 between the measuring signal and reference signal of the embodiment is advantageous in that the operation of deactivating the linker film 26 is unnecessary. The characteristics of the sensing surfaces SS1 and SS2 can be equal. This can suppress occurrence of a difference between amounts of non-specific adsorption on the sensing surfaces SS1 and SS2. Influence of the non-specific adsorption can be canceled reliably by compensation according to the measuring signal and reference signal.

In the above embodiment, the flow channels 31 and 32 are offset from one another. The passageways 31c and 32c are in the S shape. However, other shapes of the flow channels 31 and 32 may be used. For example, the passageways 31c and 32c may be straight. However, if the passageways 31c and 32c of the flow channels 31 and 32 arranged in two arrays are straight, the measuring points mp1 and mp2 are likely to offset in the width direction of the sensor unit 10. This will complicate the structure of the optical system as the light source devices must be offset from one another. Therefore, the arrangement of the flow channels 31 and 32 of the above embodiment is considerably advantageous in that the passageways 31c and 32c are in the S shape and that the measuring points mp1 and mp2 are arranged on one line.

In the above embodiment, the flow cell body 33 and the connection panels 34 are included in the flow cell 30 as a single formed piece. However, the connection panels 34 may be a plastic part originally separate from the flow cell body 33 which may be a plastic part. In this structure, at first the flow cell body 33 is placed on the prism 20. Then the connection panels 34 are fitted and squeeze the flow cell body 33 and the prism 20 together for fastening the flow cell body 33 thereto.

In the above embodiment, the assay apparatus 50 is single and operates for any of steps of the immobilization, assay and data analysis. However, plural components into which the assay apparatus 50 are split may be used for those steps. This is effective in handling a plurality of the sensor units 10 at the same time to raise efficiency in the assay.

In the above embodiment, the linker film 26 is formed on the entire surface of the thin film 25. However, the linker film 26 can be formed at least on portions of the thin film 25 for forming the sensing surfaces SS1 and SS2.

In the embodiment, the prism 20 is in the shape of the quadrilateral prism of which a section is a trapezoid. However, the prism 20 may be formed in other shapes. Examples of the shapes are a triangular prism, pentagonal prism, and other polygonal prisms, and also a semi cylindrical form which can have a light entrance surface, a light exit surface and a reflection surface of total internal reflection. In the embodiment, the prism 20 in the sensor unit 10 is for use with the assay apparatus 50. However, the prism 20 may be used in applications which are distinct from assay but in optical techniques in which total internal reflection is utilized.

In addition to the assay apparatus 50 of the above embodiment, an assay sensor unit according to the invention can be other sensors in utilizing attenuated total reflection. One example of sensor unit according to utilizing the attenuated total reflection is a leaky mode sensor. The leaky mode sensor includes a dielectric medium, a cladding layer overlaid on the dielectric medium, and an optical waveguide layer overlaid on the cladding layer, those layers constituting a thin film. A first surface of the thin film is a sensing surface on the optical waveguide layer. A second surface of the thin film is a metal/dielectric interface on the cladding layer. When light becomes incident on the metal/dielectric interface to satisfy the condition of the total reflection, part of the light passes through the cladding layer, and enters the optical waveguide layer. A guided mode to propagate light is excited responsively in the optical waveguide layer, to attenuate the reflected light on the metal/dielectric interface. An angle of the incidence at which the guided mode is excited is changeable according to the refractive index of the medium positioned on the sensing surface. This is similar to the characteristic of the resonance angle of the SPR sensor. The attenuation of the reflected light is detected, so that it is possible to measure the interaction on the sensing surface.

Unlike the above assay method in utilizing attenuated total reflection, an assay of the invention may be an assay with a sensor unit according to colorimetry. In combination, an assay apparatus for biochemical analysis may be a spectrophotometer in which color reaction of a sample is caused, and optical density of color reaction is optically measured in the colorimetry. According to this, the sensing surface of the invention can be a reaction layer for reaction between a sample and reagent. The optical block of the invention can be a panel shaped transparent support for supporting the reaction layer.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A sensor unit usable in an assay apparatus having an assay stage, comprising:
    an optical block, supported on a stage surface of said assay stage, having a sensing surface positioned on an upper surface thereof, said sensing surface receiving illuminating light applied thereto to reflect said illuminating light;
    said assay apparatus receiving said illuminating light reflected by said sensing surface, for measuring reaction of a sample;
    at least one engageable portion of a protruding or retreating shape, formed with said optical block, for keeping said optical block positioned on said stage surface by engagement with a retention mechanism of said assay apparatus.

2. A sensor unit as defined in claim 1, wherein said at least one engageable portion is two engageable portions disposed on first and second lateral faces of said optical block which are so positioned that said sensing surface is disposed between.

3. A sensor unit as defined in claim 2, wherein said optical block is in a prismatic shape which is in an inverted trapezoidal form when viewed in a section;
    said engageable portion is a ridge formed to project from a lower edge of said first and second lateral faces of said optical block extending in a block longitudinal direction.

4. A sensor unit as defined in claim 3, wherein said ridge extends consecutively in said block longitudinal direction.

5. A sensor unit as defined in claim 3, wherein said at least one engageable portion is plural engageable portions arranged in one line in said block longitudinal direction of said optical block.

6. A sensor unit as defined in claim 3, further comprising a grip portion, formed at a first end of said optical block, and adapted to holding of said optical block.

7. A sensor unit as defined in claim 1, wherein said optical block is a total reflection prism of which said upper surface is a total reflection surface.

8. A sensor unit as defined in claim 1, wherein said sensing surface is constituted by a layer of a thin film which is responsive to light applied by satisfying total reflection condition on said optical block, for attenuating intensity of reflected light thereof;
    said assay apparatus is an apparatus for assay in utilizing attenuated total reflection, and includes:
    a light source for applying said illuminating light to said sensing surface by satisfying total reflection condition; and
    a photo detector for photoelectrically detecting said illuminating light reflected by said sensing surface.

9. A total reflection prism usable in an optical apparatus having a stage, comprising:
    a prism body, shaped prismatically or semi-cylindrically, supported on a stage surface of said stage, having a total reflection surface positioned on an upper surface thereof, said total reflection surface receiving illuminating light applied thereto by a light source of said optical apparatus to reflect said illuminating light totally;
    at least one engageable portion of a protruding or retreating shape, formed with said prism body, for keeping said prism body positioned on said stage surface by engagement with a retention mechanism of said optical apparatus.

10. A total reflection prism as defined in claim 9, wherein said at least one engageable portion is two engageable portions disposed on first and second lateral faces of said prism body which are so positioned that said total reflection surface is disposed between.

11. A total reflection prism as defined in claim 9, wherein said engageable portion is a ridge extending consecutively in a body longitudinal direction of said prism body.

12. A total reflection prism as defined in claim 9, wherein said at least one engageable portion is plural engageable portions arranged in one line in a body longitudinal direction of said prism body.

* * * * *